United States Patent [19]

Shockley et al.

[11] Patent Number: 5,629,025
[45] Date of Patent: May 13, 1997

[54] LOW SODIUM PERITONEAL DIALYSIS SOLUTION

[75] Inventors: Ty R. Shockley, Highland Park; Leo Martis, Long Grove; Lee W. Henderson, Lake Forest; John Moran, Evanston, all of Ill.; Masaaki Nakayama, Tokyo, Japan

[73] Assignee: Baxter International Inc., Deerfield, Ill.

[21] Appl. No.: 423,176

[22] Filed: Apr. 18, 1995

Related U.S. Application Data

[60] Division of Ser. No. 205,304, Mar. 3, 1994, which is a continuation-in-part of Ser. No. 130,968, Oct. 4, 1993, abandoned.

[51] Int. Cl.$^6$ .......... A61K 31/195; A61K 31/70; A61K 33/10; A61K 33/14
[52] U.S. Cl. .......... 424/680; 424/678; 424/681; 424/682; 424/686; 424/717; 514/23; 514/557; 514/561
[58] Field of Search .......... 424/678, 679, 424/680, 681, 682, 686, 663, 717; 514/23, 557, 561

[56] References Cited

U.S. PATENT DOCUMENTS

| | | | |
|---|---|---|---|
| 4,404,192 | 9/1983 | Suzuki | 424/153 |
| 4,489,535 | 12/1984 | Veltman | 53/431 |
| 4,663,166 | 5/1987 | Veech | 424/146 |
| 4,663,289 | 5/1987 | Veech | 435/240 |
| 4,668,400 | 5/1987 | Veech | 210/647 |
| 4,722,798 | 2/1988 | Goss | 210/646 |
| 5,032,615 | 7/1991 | Ward et al. | 514/574 |
| 5,091,094 | 2/1992 | Veech | 210/647 |
| 5,211,643 | 5/1993 | Reinhardt et al. | 604/416 |

OTHER PUBLICATIONS

Nakayama, *Studies on the Sodium Concentration of Dialysate for Continuous Ambulatory Peritoneal Dialysis*, Japanese Journal of Nephrology, 34(8):913–20 (Aug. 1992).
Nakayama, *Clinical Effect of Low Na Concentration Dialysate (120 mEq/L) for CAPD Patients*, PD Conference, San Diego, CA (Mar. 1993).
Twardowski et al., Nephron 42:93–101 (1986).

*Primary Examiner*—Phyllis G. Spivack
*Attorney, Agent, or Firm*—Thomas S. Borecki; Charles R. Mattenson; Robert M. Barrett

[57] ABSTRACT

An improved peritoneal dialysis solution comprising an osmotic agent having at least one amino acid, and a method of administering same to a patient are provided. Pursuant to the present invention, the sodium concentration in the solution is decreased thus causing sodium to be transported from the circulation to the peritoneal cavity. This provides for an improved ultrafiltration profile that is, more volume over a longer period of time, for the same initial osmolality when compared to standard solutions. Also, the same ultrafiltration profile as standard solutions can be achieved with lower initial osmolalities.

9 Claims, 5 Drawing Sheets

LOW SODIUM PERITONEAL DIALYSIS SOLUTION

This is a division of application Ser. No. 08/205,304, filed on Mar. 3, 1994, allowed which is a continuation-in-part of U.S. Ser. No. 08/130,968, filed Oct. 4, 1993 abandoned.

BACKGROUND OF THE INVENTION

The present invention relates generally to peritoneal dialysis. More specifically, the present invention relates to peritoneal dialysis solutions.

It is known to use dialysis to support a patient whose renal function has decreased to the point where the kidneys no longer sufficiently function. Two principal dialysis methods are utilized: hemodialysis; and peritoneal dialysis.

In hemodialysis, the patients blood is passed through an artificial kidney dialysis machine. A membrane in the machine acts as an artificial kidney for cleansing the blood. Because it is an extracorporeal treatment that requires special machinery, there are certain inherent disadvantages with hemodialysis.

To overcome the disadvantages associated with hemodialysis, peritoneal dialysis was developed. Peritoneal dialysis utilizes the patient's own peritoneum as a semipermeable membrane. The peritoneum is the membranous lining of the abdominal cavity that due to a large number of blood vessels and capillaries is capable of acting as a natural semi-permeable membrane.

In peritoneal dialysis, a dialysis solution is introduced into the peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. This allows the proper acid-base electrolyte and fluid balance to be returned to the blood and the dialysis solution is simply drained from the body cavity through the catheter.

Although many advantages to peritoneal dialysis exist, one of the difficulties that has been encountered is providing a suitable amount of osmotic agent. What is required is achieving a sufficient osmotic gradient. The osmotic agent is used in a dialysis solution to maintain the osmotic gradient that is required to cause the transport of water and its accompanying toxic substances across the peritoneum into the dialysis solution.

Using dextrose as an osmotic agent is known. Dextrose is fairly safe and is readily metabolized if it enters the blood. However, one of the issues with respect to dextrose is that due to its small size, it is rapidly transported from the peritoneal cavity. Because dextrose crosses the peritoneum so rapidly, the osmotic gradient is dissipated within two to three hours of infusion, leading to the loss of ultrafiltration.

A disadvantage of the rapid uptake of glucose by the blood is that it can represent a large proportion of the patient's energy intake. With respect to, for example a diabetic patient, this can represent a severe metabolic burden to a patient whose glucose tolerance is already impaired. Dextrose can also cause problems with respect to hyperglycemia and obesity.

Typical peritoneal dialysis solutions contain sodium in a concentration of 132 mEq/L and dextrose at a concentration of 1.5 to 4.25% by weight. The solutions rely on a high initial solution osmolality to affect the transport of water (metabolic waste products) from the circulation to the peritoneal cavity. Such a solution results in a daily absorption of 150 to 300 grams of glucose from the dialysate in the typical peritoneal dialysis patient.

Further, with respect to the sodium levels, most hypertensive end stage renal patients are volume and sodium overloaded. Current peritoneal dialysis solutions do not adequately control blood pressure, because among other things they do not remove enough sodium. Still further, an issue arises with respect to fluid intake because renal patients must control their fluid intake.

Therefore, a need exists for an improved peritoneal dialysis solution.

SUMMARY OF THE INVENTION

The present invention provides an improved peritoneal dialysis solution. Pursuant to the present invention, the sodium concentration in the solution is decreased to below the patient's plasma concentrations of sodium, thus causing sodium to be transported from the circulation to the peritoneal cavity. This yields an increased ultrafiltration volume for the same initial osmolality. Pursuant to the present invention, a reduced amount of osmotic agent can be used to achieve equivalent ultrafiltration.

To this end, a peritoneal dialysis solution comprising an osmotic agent and sodium in a concentration that is less than a sodium plasma concentration in the patient is provided. The osmotic agent is chosen from the group consisting of: amino acids; polypeptides; polyglucose; and glycerol.

In an embodiment, the peritoneal dialysis solution generally comprises 0 to about 200 (mOsm/L) of an osmotic agent and includes:

0.0 to about 4.0 (% w/v) dextrose;

0 to about 120 (meq/L) sodium;

0 to about 100 (meq/L) chloride;

0 to about 45 (meq/L) lactate;

0 to about 45 (meq/L) bicarbonate;

0.0 to about 4.0 (meq/L) calcium; and 0.0 to about 4.0 (meq/L) magnesium.

In an embodiment, the peritoneal dialysis solution has a total osmolality of 300 to about 500.

In an embodiment of the peritoneal dialysis solution, the sodium comprises approximately 35 to about 125 (meq/L).

In a further embodiment, the present invention provides a method for manufacturing a peritoneal dialysis solution comprising the steps of reducing the concentration of sodium present in the solution below 132 (meq/L) to cause an equivalent ultrafiltration volume with a reduced initial solution osmolality (when compared to normal peritoneal dialysis fluid) or an increased ultrafiltration volume with the same initial solution osmolality (when compared to normal peritoneal dialysis fluid).

In another embodiment, the present invention provides a method for providing peritoneal dialysis to a patient comprising the steps of administering a solution including sodium and an osmotic agent chosen from the group consisting of polypeptides, polyglucose, amino acids and glycerol. The sodium level is less than a plasma sodium concentration of the patient to cause an equivalent ultrafiltration volume with a reduced initial solution osmolality (when compared to normal peritoneal dialysis fluid) or an increased ultrafiltration volume with the same initial solution osmolality (when compared to normal peritoneal dialysis fluid).

In yet another embodiment, the present invention provides a method for reducing hypertension in a dialysis patient at risk of same. The method includes the step of administering to a hypertensive dialysis patient a peritoneal dialysis solution including an osmotic agent and sodium in a concentration that is less than a sodium concentration in the hypertensive dialysis patient who is to receive the solution.

The peritoneal dialysis solution can be designed to be used in a patient who receives only one dwell a day of the low sodium solution or multiple dwells a day.

An advantage of the present invention is to provide an improved peritoneal dialysis solution.

Still further, an advantage of the present invention is to provide an improved method for providing dialysis to a patient.

A further advantage of the present invention is to provide a peritoneal dialysis solution with lower sodium concentrations that provides ultrafiltration over a longer period of time for the same starting osmolality.

Furthermore, an advantage of the present invention is to provide a peritoneal dialysis solution which provides a decreased glucose load to the patient.

Another advantage of the present invention is to provide a peritoneal dialysis solution with reduced sodium concentrations.

Still further, an advantage of the present invention is to provide a peritoneal dialysis solution with lower sodium concentrations used in combination with dextrose, that achieves comparable ultrafiltration profiles at lower initial osmolalities.

Moreover, an advantage of the present invention is to provide a peritoneal dialysis solution that helps to preserve the normal functions of peritoneal cells such as macrophages, fibroblasts and mesothelial cells.

Additionally, an advantage of the present invention is to provide a peritoneal dialysis solution with an increased ultrafiltration volume and an improved volume profile.

Another advantage of the present invention is to provide a peritoneal dialysis solution that can be used for the overnight dwell in Continuous Ambulatory Peritoneal Dialysis (CAPD).

Still further, an advantage of the present invention is to provide a peritoneal dialysis solution that will increase the amount of sodium that is removed from the patient.

Furthermore, an advantage of the present invention is to provide a peritoneal dialysis solution that will reduce patient's fluid intake.

Yet another advantage of the present invention is to provide an intraperitoneal solution that can improve the management of blood pressure and fluid volume for congestive heart disease patients.

Another advantage of the present invention is to provide a peritoneal dialysis solution that can be used advantageously for Automated Peritoneal Dialysis (APD).

Moreover, another advantage of the present invention is to provide a peritoneal dialysis solution that may be used to correct overhydration of a patient.

Yet another advantage of the present invention is to provide a peritoneal dialysis solution that may be used to control hypertension.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides an improved peritoneal dialysis solution that contains a reduced sodium concentration, less than 132 meq/L. In a preferred embodiment, the sodium concentration is present in an amount equal to or less than 120 mEq/L. The concentration of sodium is lower than the normal plasma sodium concentration of the patient (140–145 mmol/L), and thus sodium is transported from the circulation to the peritoneal cavity. Unexpectedly, an increased ultrafiltration volume and an improved volume profile with time may be achieved pursuant to the present invention with a low sodium peritoneal dialysis solution having the same initial osmolality as compared to a solution having a more conventional sodium concentration.

Figure 1:
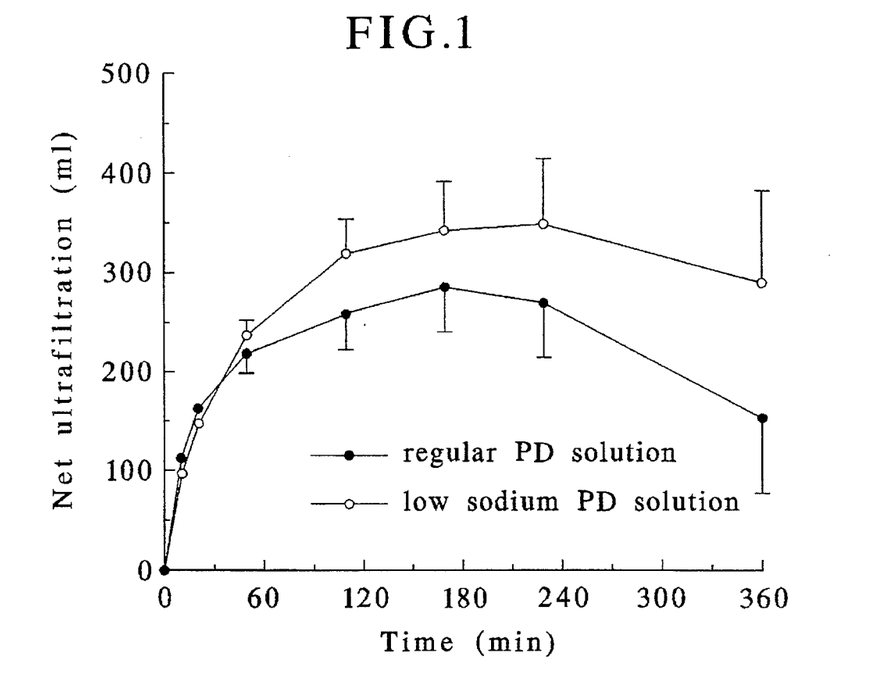
FIG. 1 illustrates, graphically, net ultrafiltration versus time for a typical peritoneal dialysis solution and one constructed pursuant to the present invention, both solutions having the same initial osmolality.

As illustrated in FIG. 1 (which will be discussed in more detail infra), dialysis with the low sodium solution of the present invention, having the same initial osmolality as a solution with more conventional sodium concentrations unexpectedly results in an increased ultrafiltration volume and a sustained volume profile with time. Additionally, using the low sodium solution of the present invention provides for an increased removal of sodium from the patient. The increased ultrafiltration profile is observed to occur even though the dialysate osmolalities of both solutions remains the same (see FIG. 2 discussed in more detail infra).

Pursuant to the present invention, any osmotic agent can be used in the solution. For example, dextrose, glycerol, polyglucose, polypeptides and amino acids can be used as the osmotic agent. It is envisioned, that the peritoneal dialysis solution of the present invention with reduced sodium concentrations can be used with unique advantages for the following applications: for fluid overloaded patients; for sodium overloaded patients; for patients with ultrafiltration failure; for hypertensive patients; with high molecular weight osmotic agents to decrease glucose load and osmolality; for long dwells—greater than six hours for example APD daytime dwell and CAPD overnight dwell; and for chronic congestive heart failure patients.

It has been found that if glucose is used as the osmotic agent that the glucose load to the CAPD (continuous ambulatory peritoneal dialysis) or APD (automated peritoneal dialysis) patient can be reduced with a low sodium concentration. This is because when a low sodium concentration is used in combination with dextrose, one can achieve ultrafiltration profiles comparable to a typically higher dextrose solution. Indeed, dextrose can be eliminated when the low sodium concentration solution is used in combination with other osmotic agents such as glycerol, polyglucose, polypeptides, and amino acids.

Additionally, the use of peritoneal dialysis solutions with low sodium concentrations causes the transport of sodium and its counter ion from the circulation to the peritoneal cavity. Thus, when used in combination with a larger, slower transporting osmotic agent (polypeptides, polyglucose, etc.) the ultrafiltration profile will be flatter. In this regard, the osmotic gradient will be maintained for longer periods of time. Thus, solutions of this kind are advantageous for longer dwells such as CAPD overnight or APD daytime dwells.

FIG. 1 illustrates actual net ultrafiltration in patients, over time, of a typical peritoneal dialysis solution and a solution constructed pursuant to the present invention pursuant to the protocol set forth in the experiment infra. FIG. 1 demonstrates the increased ultrafiltration volume and sustained volume achieved with the present invention.

It has been noted that higher initial osmolalities of current peritoneal dialysis solutions can impair host defense mechanisms against infection by suppressing the normal functions of peritoneal cells (macrophages, fibroblasts, mesothelial cells). An advantage of the present invention is that when low sodium concentrations are used in combination with dextrose, comparable ultrafiltration profiles can be achieved at a lower initial osmolality; this thus assists in restoring the normal functions of peritoneal cells.

Another advantage of the present invention is that a low sodium concentration will increase the amount of sodium that is removed from the patient. The low sodium solution of the present invention increases the amount of sodium that is removed from the patient. By removing more sodium, the renal patient's restrictions on salt intake can be relaxed. Thus, renal patients could include more salt in their diet which would tend to increase protein intake and thus, an improved nutritional status.

The peritoneal dialysis solution of the present invention can generally have a profile such as follows:

Solution containing dextrose composition:

| | |
|---|---|
| Dextrose (% w/v) | 0.0–4.0 |
| Sodium (mEq/L) | 0–130 |
| Chloride (Meq/L) | 0–100 |
| Lactate (mEq/L) | 0–45 |
| Bicarbonate (mEq/L) | 0–45 |
| Calcium (mEq/L) | 0.0–4.0 |
| Magnesium (mEq/L) | 0.0–4.0 |
| Total osmolality (mOsm/L) | 300–500 |

Solution containing an osmotic agent other than dextrose composition:

| | |
|---|---|
| Osmotic agent (mOsm/L) | 0–200 |
| Sodium (mEq/L) | 0–130 |
| Chloride (mEq/L) | 0–100 |
| Lactate (mEq/L) | 0–45 |
| Bicarbonate (mEq/L) | 0–45 |
| Calcium (mEq/L) | 0.0–4.0 |
| Magnesium (mEq/L) | 0.0–4.0 |
| Total osmolality (mOsm/L) | 300–500 |

More specifically, the peritoneal dialysis solutions have preferred ranges as follows:

Composition Ranges for Low Sodium Solutions Used for All Dwells

Solution containing dextrose:

| | |
|---|---|
| Dextrose (% w/v) | 1.0–4.0 |
| Sodium (mEq/L) | 90–130 |
| Chloride (mEq/L) | 39–95 |
| Combination of Lactate and Bicarbonate (mEq/L) | 30–45 |
| Calcium (mEq/L) | 0.0–4.0 |
| Magnesium (mEq/L) | 0.0–2.0 |
| Total Osmolality (mOsm/L) | 300–500 |

Solution containing an osmotic agent other than dextrose or containing dextrose in combination with another osmotic agent:

| | |
|---|---|
| Osmotic Agent (mOsm/L) | 1–200 |
| Dextrose (% w/v) | 1.0–4.0 |
| Sodium (mEq/L) | 90–130 |
| Chloride (mEq/L) | 39–95 |
| Combination of Lactate and Bicarbonate (mEq/L) | 30–45 |
| Calcium (mEq/L) | 0.0–4.0 |
| Magnesium (mEq/L) | 0.0–2.0 |
| Total Osmolality (mOsm/L) | 300–500 |

Composition Ranges for Low Sodium Solutions Used for Only One Dwell per Day

Solution containing dextrose:

| | |
|---|---|
| Dextrose (% w/v) | 1.0–4.0 |
| Sodium (mEq/L) | 35–120 |
| Chloride (mEq/L) | 0–85 |
| Combination of Lactate and Bicarbonate (mEq/L) | 30–45 |
| Calcium (mEq/L) | 0.0–4.0 |
| Magnesium (mEq/L) | 0.0–2.0 |

| Total Osmolality (mOsm/L) | 300–500 |

Solution containing an osmotic agent other than dextrose or containing dextrose in combination with another osmotic agent:

| | |
|---|---|
| Osmotic agent (mOsm/L) | 1–200 |
| Dextrose (% w/v) | 1.0–4.0 |
| Sodium (mEq/L) | 35–85 |
| Chloride (mEq/L) | 0–100 |
| Combination of Lactate and Bicarbonate (mEq/L) | 30–45 |
| Calcium (mEq/L) | 0.0–4.0 |
| Magnesium (mEq/L) | 0.0–4.0 |
| Total Osmolality (mOsm/L) | 300–500 |

Preferred Composition Ranges for Low Sodium Solutions Used for All Dwells

Sodium containing dextrose with the following composition:

| | |
|---|---|
| Dextrose (% w/v) | 1.0–4.0 |
| Sodium (mEq/L) | 100–125 |
| Chloride (mEq/L) | 55–87 |
| Combination of Lactate and Bicarbonate (mEq/L) | 35–40 |
| Calcium (mEq/L) | 2.5–3.5 |
| Magnesium (mEq/L) | 0.5–1.5 |
| Total osmolality (mOsm/L) | 300–500 |

Solution containing an osmotic agent other than dextrose or containing dextrose in combination with another osmotic agent:

| | |
|---|---|
| Osmotic agent (mOsm/L) | 1–200 |
| Dextrose (% w/v) | 1.0–4.0 |
| Sodium (mEq/L) | 100–125 |
| Chloride (mEq/L) | 55–87 |
| Combination of Lactate and Bicarbonate (mEq/L) | 35–40 |
| Calcium (mEq/L) | 2.5–3.5 |
| Magnesium (mEq/L) | 0.5–1.5 |
| Total Osmolality (mOsm/L) | 300–500 |

Preferred Composition Ranges for Low Sodium Solutions Used for One Dwell per Day Solution containing dextrose:

| | |
|---|---|
| Dextrose (% w/v) | 1.0–4.0 |
| Sodium (mEq/L) | 35–120 |
| Chloride (mEq/L) | 3–82 |
| Combination of Lactate and Bicarbonate (mEq/L) | 35–40 |
| Calcium (mEq/L) | 2.5–3.5 |
| Magnesium (mEq/L) | 0.5–1.5 |
| Total Osmolality (mOsm/L) | 300–500 |

Solution containing an osmotic agent other than dextrose or containing dextrose in combination with another osmotic agent:

| | |
|---|---|
| Osmotic agent (mOsm/L) | 1–200 |
| Dextrose (% w/v) | 1.0–4.0 |
| Sodium (mEq/L) | 35–120 |
| Chloride (mEq/L) | 3–82 |
| Combination of Lactate and Bicarbonate (mEq/L) | 35–40 |
| Calcium (mEq/L) | 2.5–35 |
| Magnesium (mEq/L) | 0.5–15 |
| Total Osmolality (mOsm/L) | 300–500 |

By way of example, and not limitation, specific examples of peritoneal solutions of the present invention are as follows:

Examples of Specific Compositions for Low Sodium PD Solutions

TABLE No. 1

| Solution | Dextrose (% w/v) | Sodium (mEq/L) | Lactate (mEq/L) | Chloride (mEq/L) | Calcium (mEq/L) | Magnesium (mEq/L) | Total Osm (mOsmol/L) |
|---|---|---|---|---|---|---|---|
| 1 | 1.5 | 100 | 40 | 63 | 2.5 | 0.5 | 280 |
| 2 | 1.5 | 110 | 40 | 73 | 2.5 | 0.5 | 300 |
| 3 | 1.5 | 120 | 40 | 83 | 2.5 | 0.5 | 320 |
| 4 | 1.5 | 125 | 40 | 88 | 2.5 | 0.5 | 330 |
| 5 | 2.5 | 100 | 40 | 63 | 2.5 | 0.5 | 331 |
| 6 | 2.5 | 105 | 40 | 69 | 3.5 | 0.5 | 342 |
| 7 | 2.5 | 110 | 40 | 73 | 2.5 | 0.5 | 351 |
| 8 | 2.5 | 120 | 40 | 83 | 2.5 | 0.5 | 371 |
| 9 | 2.5 | 125 | 10 | 88 | 2.5 | 0.5 | 381 |
| 10 | 2 | 100 | 40 | 63 | 2.5 | 0.5 | 306 |
| 11 | 2 | 110 | 40 | 73 | 2.5 | 0.5 | 926 |
| 12 | 2 | 120 | 40 | 83 | 2.5 | 0.5 | 348 |
| 13 | 2 | 125 | 40 | 88 | 2.5 | 0.5 | 356 |
| 14 | 3 | 100 | 40 | 63 | 2.5 | 0.5 | 358 |
| 15 | 3 | 110 | 40 | 73 | 2.5 | 0.5 | 376 |

TABLE No. 1-continued

| Solution | Dextrose (% w/v) | Sodium (mEq/L) | Lactate (mEq/L) | Chloride (mEq/L) | Calcium (mEq/L) | Magnesium (mEq/L) | Total Osm (mOsmol/L) |
|---|---|---|---|---|---|---|---|
| 16 | 3 | 125 | 40 | 83 | 2.5 | 0.5 | 396 |
| 17 | 3 | 125 | 40 | 88 | 2.5 | 0.5 | 406 |
| 18 | 2.2 | 115 | 40 | 78 | 2.5 | 0.5 | 346 |
| 19 | 2.8 | 100 | 40 | 63 | 2.5 | 0.5 | 346 |
| 20 | 3.6 | 100 | 35 | 70 | 3.5 | 1.5 | 389 |

By way of example, and not limitation, experiments using the present invention will now be given:

Experiment #1

The effects of low sodium concentration dialysates and normal sodium concentration dialysate, on the peritoneal fluid, sodium transport, the extracellular volumes and plasma volume in CAPD patients was evaluated.

STUDY PRODUCTS

Trial product (ULNaD)

Two liters of peritoneal dialysis solution with:

(1) sodium=100 mEq/l, calcium=3.5 mEq/l, magnesium= 1.5 mEq/l, chloride=70 mEq/l, lactate=35 mmol/l, glucose=180 mmol/l, dextran 70=1 g/l, (2) osmolarity=384 mOsmol/l.

Control solution (NNAD)

Two liters of commercially available peritoneal dialysis solution (Dianeal® 2.5%) with:

(1) sodium=182 mEq/l, calcium=3.5 mEq/l, magnesium= 1.5 mEq/l, chloride=102 mEq/l, lactate=35 mmol/l, glucose=126 mmol/l, dextran=70 1 g/l, (2) osmolarity=384 mOsmol/l.

STUDY DESIGN

Six stable CAPD patients were randomized in 2 groups of 3 patients. Two peritoneal permeability tests with a duration of 6 hrs were performed within one week in all patients. One group of patients was investigated using the trial solution on the first examination, the other group with the control solution during the first test. The other solution was used during the second test, allowing paired observations.

Before instillation of the trial/control solution, the peritoneal cavity was rinsed with dialysate with the trial solution when the trial solution was used and with the control solution when the control solution was used. Dialysate samples were taken before instillation and 10, 20, 30, 60, 120, 180, 240, and 360 minutes after instillation of the test solution. Blood samples were taken at: −1080, −1070, 0, 60, 120, 180, 240 and 360 minutes. At −1080 minutes (18 hrs before the test) inulin (Inntest®) (60 mg/kg) was given intravenously to measure extracellular volume and plasma volume. At t=0 minutes, 20 ml dextran 1 (Promitan®) (150 mg/ml) was given to prevent an anaphylactic reaction on dextran 70. At the end of the dwell period, the peritoneal cavity was rinsed once (control or trial solution) to allow calculation of the residual volume after drainage. All patients were provided with a standard meal of=1000 mg sodium and 500 calories before the test dwell.

STUDY PROCEDURES

A. Patient selection

Criteria for selection a. Aged at least 18 years b. Patients established on CAPD for at least 8 months Criteria for exclusion a. Patients with peritonitis, or receiving antibiotics for peritonitis, within the previous 30 days.

b. Patients with an allergic reaction on dextran during previous examinations.

c. Patients with congestive heart failure.

Laboratory a. Parameters of plasma/blood

Inulin, sodium, potassium, chloride, calcium, magnesium, total protein, hemoglobin, hematocrit, glucose, urea, creatinine, urate, osmolarity, dextran antibodies, $\beta_2$-microglobulin, albumin, transferring, IgG, IgA, and $\alpha_2$-macroglobulin.

b. Parameters of dialysate

Volume, inulin, sodium, potassium, chloride, calcium, magnesium, glucose, urea, creatinine, urate, osmolarity, $\beta_2$-microglobulin, albumin, transferrin, IgG, IgA and $\alpha_2$-macroglobulin c. Parameters of urine Urinary production at −1080, from −1080 to 0 and from 0 to 240 minutes. Inulin, sodium, potassium, creatinine.

Results

The Figures illustrate the results of the study.

FIG. 1: Net ultrafiltration as a function of time. Results obtained from 6 patients tested with both a regular PD solution (filled circles) and a low sodium PD solution having the same initial osmolality (empty circles). Concentrations of glucose and sodium in these solutions are outlined in the following table:

| Solute | Regular | Low Sodium |
|---|---|---|
| Glucose (mOsm/L) | 126 | 180 |
| Sodium (mOsm/L) | 132 | 100 |
| Total Osm (mOsm/L) | 384 | 384 |

Figure 2:
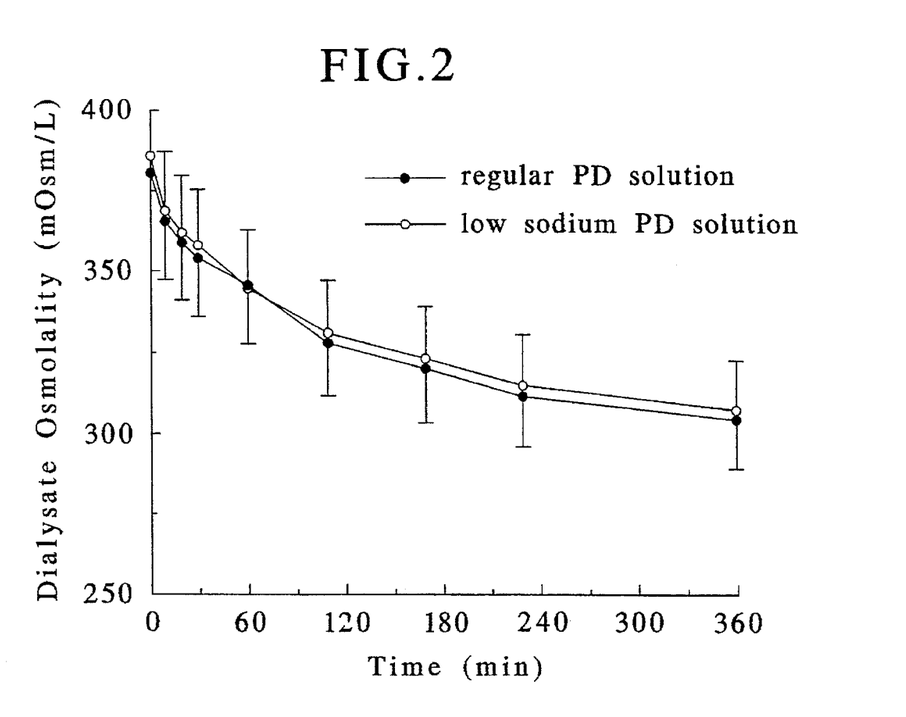
FIG. 2 illustrates, graphically, dialysate osmolality versus time for a typical peritoneal dialysis solution and one constructed pursuant to the present invention, both solutions having the same initial osmolality.

FIG. 2: Dialysate osmolalities as a function of time. Results obtained from 6 patients tested with both a regular PD solution (filled circles) and a low sodium PD solution having the same initial osmolality (empty circles). Glucose and sodium concentrations are the same as shown in the table above.

Experiment #2

The effects of using low sodium concentration dialysates instead of normal sodium concentration dialysate in hypertensive patients was evaluated.

Table 2 below sets forth the nine patients evaluated in this experiment. All of the patients were hypertensive and four of them were taking anti-hypertensive drugs at the time of this experiment. Daily salt intakes were 7–10 grams. Prior to the experiment, the patients were using standard dialysate exchanging four bags daily.

Figure 12:
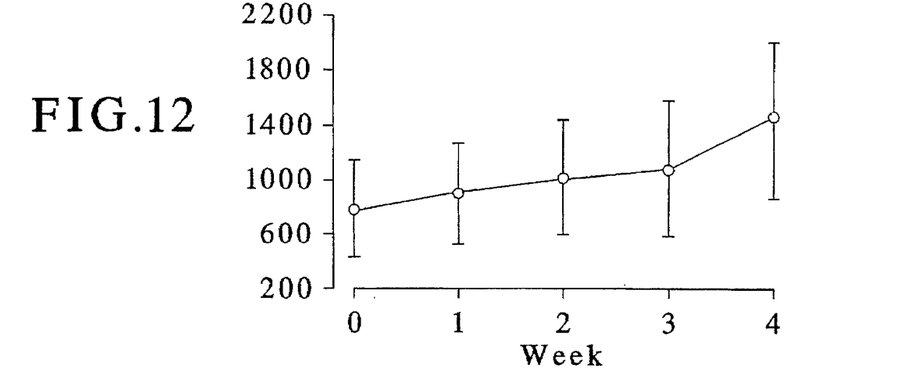
FIG. 12 illustrates, graphically, plasma aldosterone (PAC) measured in pg/ml for the patients evaluated in accordance with Experiment No. 2.
Figure 13:
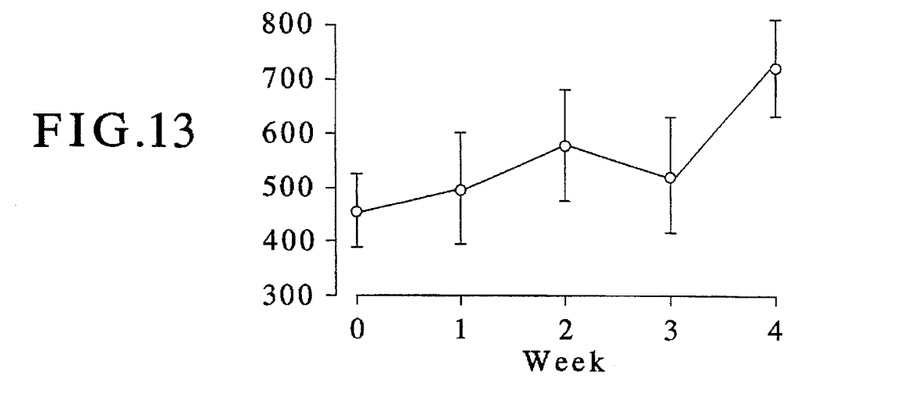
FIG. 13 illustrates, graphically, plasma norepinephrine (NEp) measured in pg/ml for the patients evaluated in accordance with Experiment No. 2.
Figure 14:
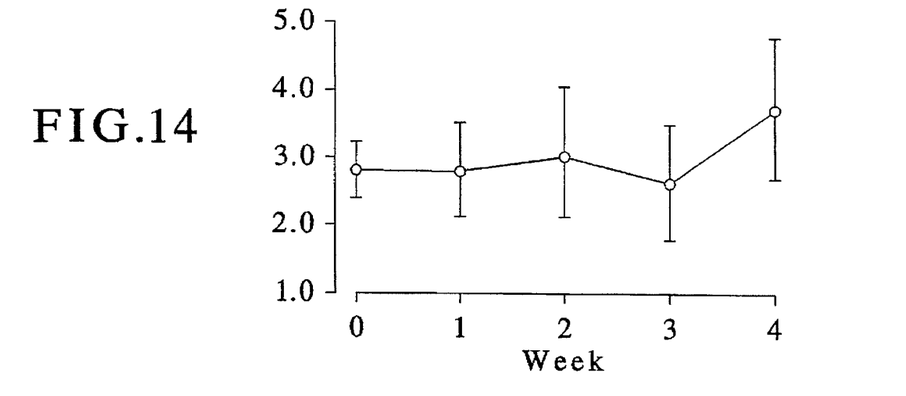
FIG. 14 illustrates, graphically, plasma vasopressin (AVP) measured in pg/ml for the patients evaluated in accordance with Experiment No. 2.

No statistical changes were found in PAC, NEp and AVP levels during the study (See FIGS. 12–14).

After starting the study, six of the patients noticed a decrease of dry mouth, which felt comfortable. Therefore, they found that water intake was decreased. Facial and leg

TABLE 2

| No | Sex | Age | CAPD(m) | UV(ml/day) | standard dialysate | low Na dialysate | study(w) |
|----|-----|-----|---------|------------|--------------------|-----------------|----------|
| 1 | M | 51 | 40 CGN | 0 | 2.5% Dx4 | 2.5% Dx4 | 1 |
| 2 | M | 60 | 28 DM | 200 | 2.5% Dx4 | 2.5% Dx4 | 2 |
| 3 | F | 40 | 4 CGN | 1000 | 1.5% Dx4 | 1.5% Dx4 | 4 |
| 4 | M | 43 | 29 CGN | 350 | 1.5% Dx3 + 4.25% Dx1 | 1.5% Dx1 + 2.5% Dx3 | 4 |
| 5 | F | 48 | 15 CGN | 200 | 1.5% Dx2 + 2.5% Dx2 | 1.5% Dx1 + 2.5% Dx3 | 4 |
| 6 | M | 34 | 12 CGN | 350 | 2.5% Dx4 | 2.5% Dx4 | 4 |
| 7 | M | 34 | 22 CGN | 1000 | 1.5% Dx2 + 2.5% Dx2 | 1.5% Dx2 + 2.5% Dx2 | 4 |
| 8 | M | 46 | 65 CGN | 0 | 1.5% Dx1 + 2.5% Dx3 | 1.5% Dx1 + 2.5% Dx3 | 4 |
| 9 | M | 32 | 7 CGN | 800 | 1.5% Dx3 + 2.5% Dx1 | 1.5% Dx3 + 2.5% Dx1 | 4 |

Method

Low sodium dialysate (120 mEq/l) was used four times daily up to four weeks, instead of standard dialysate. Body wt (kg), total drainaged volume (TDV:ml/day) and blood pressure (BP:mmHg) were measured daily. Total daily transperitoneal sodium removals (Na removal:MEq/day) were measured before and the last day of the study. Blood samples were taken every week for the measurement of serum sodium levels (mEq/l), plasma osmolality (mOsm/kgH2O) and vasoactive humoral factors, which were plasma atrial natriuretic peptide (ANP:pg/ml), plasma renin activity (PRA:ng/ml/hr), plasma aldosterone (PAC:pg/ml), plasma norepinephrine (NEp:pg/ml), plasma vasopressin (AVP:pg/ml) and c-GMP(pg/ml). BP was measured at the resting supine position in the early morning. Blood was withdrawn at the time of out-patients clinic, after lying on the bed more than 15 min.

Subjective symptoms and objective signs were examined at the out-patients clinic every week.

Results

Figure 3:
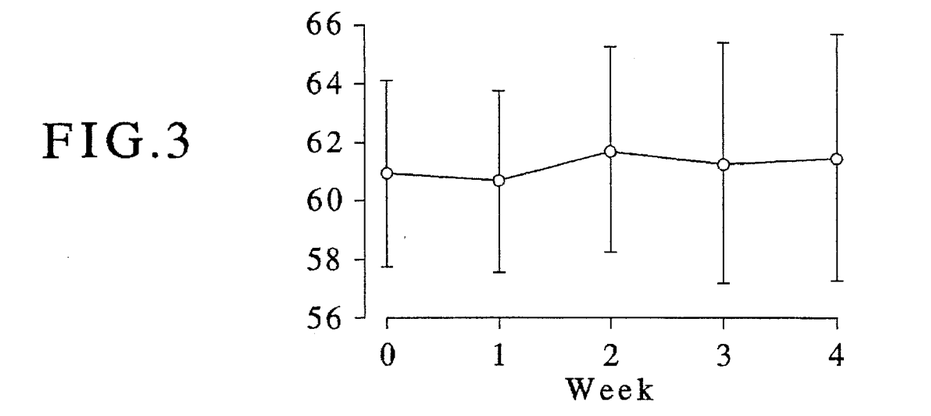
FIG. 3 illustrates, graphically, the body weight results for the patients evaluated in accordance with Experiment No. 2.
Figure 4:
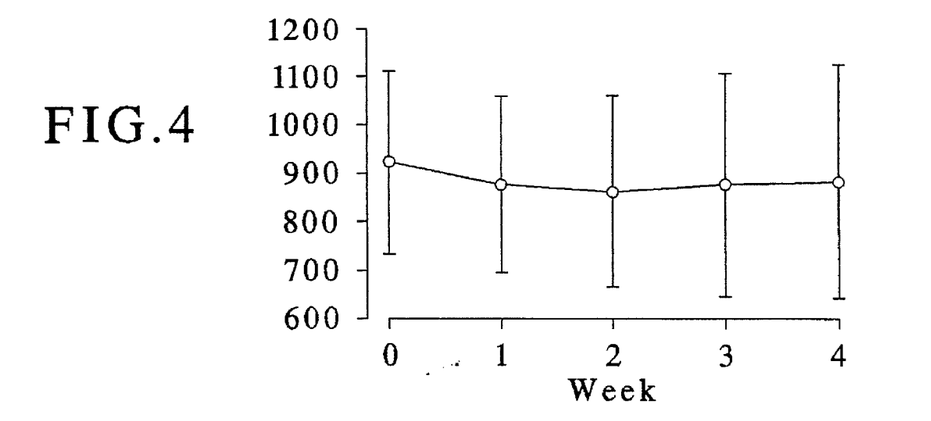
FIG. 4 illustrates, graphically, total drainage volume (TDV) measured in ml/day for the patients evaluated in accordance with Experiment No. 2.
Figure 5:
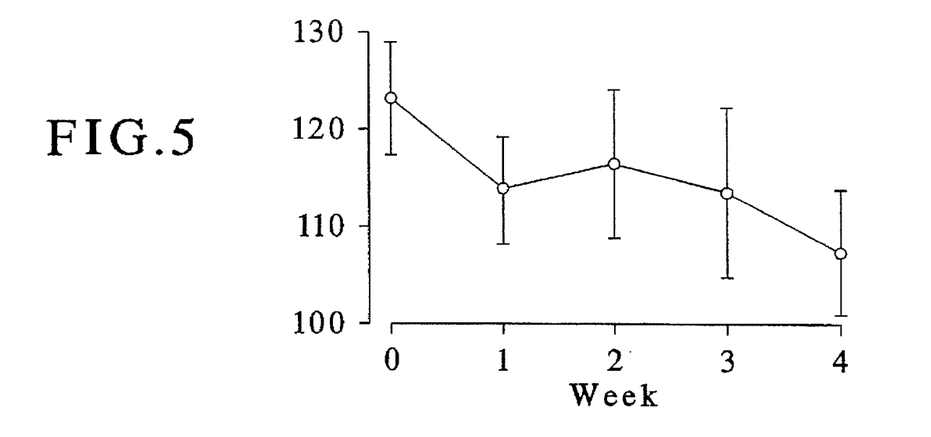
FIG. 5 illustrates, graphically, blood pressure (BP) measured in mmHg for the patients evaluated in accordance with Experiment No. 2.
Figure 6:
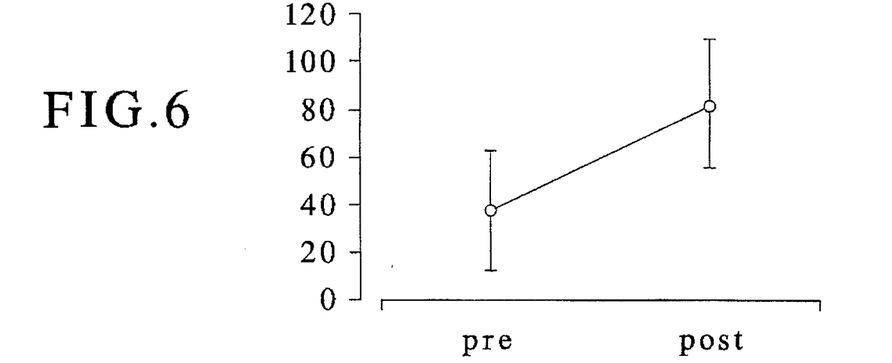
FIG. 6 illustrates, graphically, trans-peritoneal sodium removal measured in mEq/day for patients evaluated in accordance with Experiment No. 2.
Figure 7:
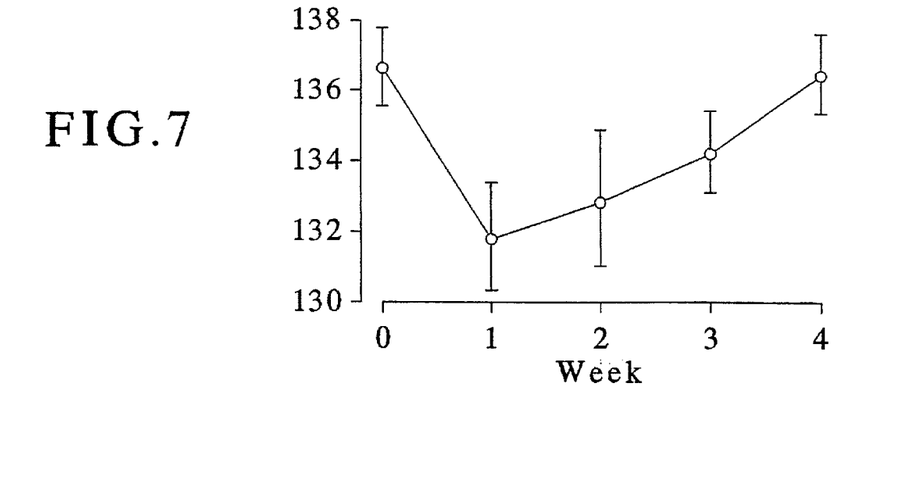
FIG. 7 illustrates, graphically, serum sodium levels measured in mEq/l for the patients evaluated in accordance with Experiment No. 2.
Figure 8:
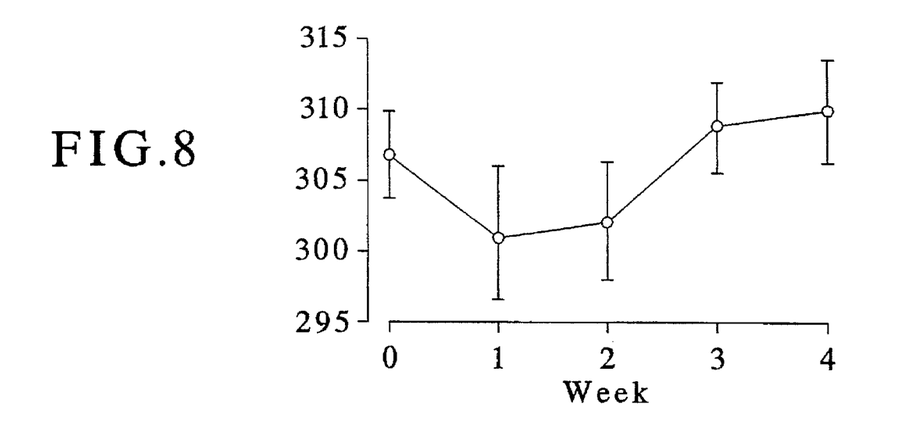
FIG. 8 illustrates, graphically, plasma osmolality measured in mOsm/kg $H_2O$ for the patients evaluated in accordance with Experiment No. 2.
Figure 9:
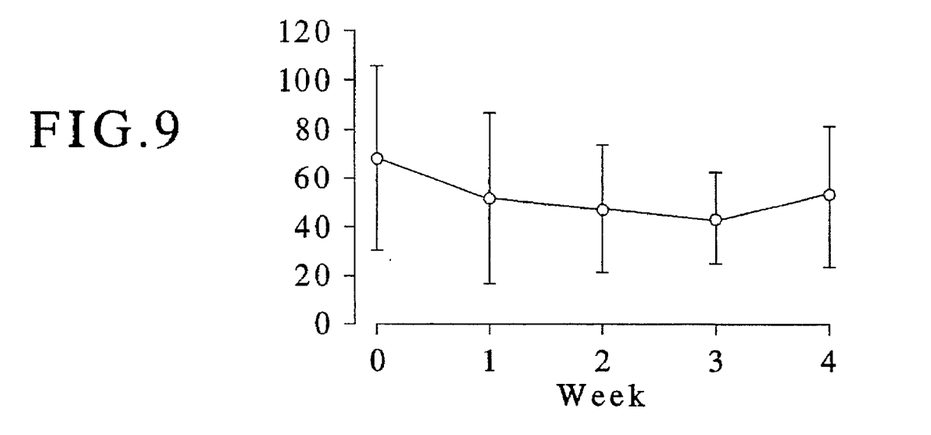
FIG. 9 illustrates, graphically, plasma atrial natriuretic peptide (ANP) measured in pg/ml for the patients evaluated in accordance with Experiment No. 2.
Figure 10:
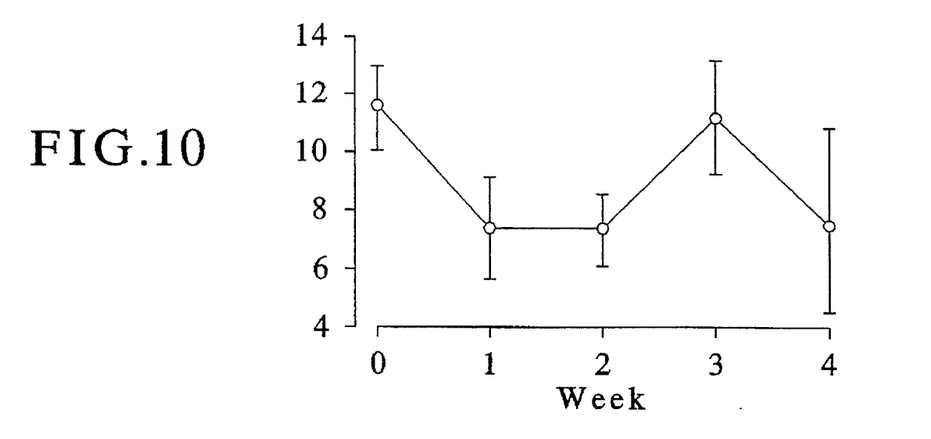
FIG. 10 illustrates, graphically, levels of c-GMP measured in pg/ml for the patients evaluated in accordance with Experiment No. 2.
Figure 11:
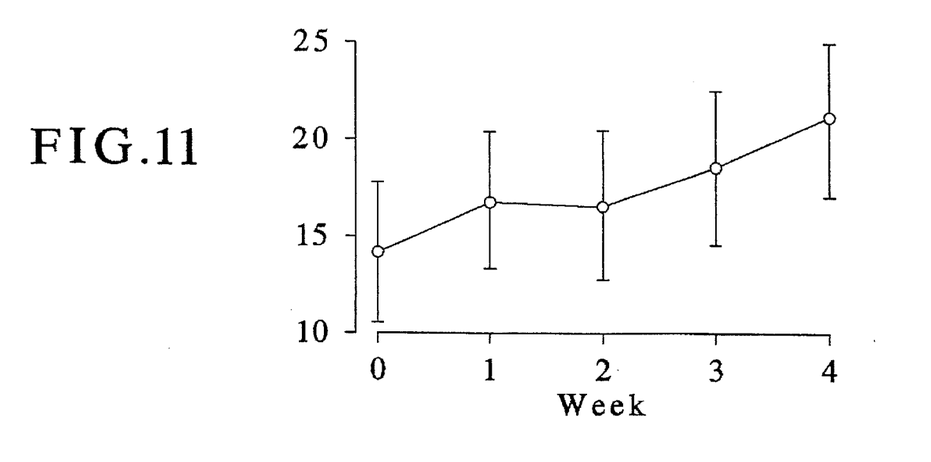
FIG. 11 illustrates, graphically, plasma atrial activity (PRA) measured in ng/ml/hr for the patients evaluated in accordance with Experiment No. 2.

Two patients were dropped out of the study, before the expiration of four weeks, because of overhydration due to inadequate ultrafiltration (patient No. 1), and progression of general fatigue due to hyponatremia (patient No. 2). The other seven cases used low sodium dialysate for four weeks without any adverse symptoms. During the study periods, no changes were found in body weight (See FIG. 3). TDV decreased in all cases compared to the pre-values, although the decreases were not significant statistically (See FIG. 4). Significant fall in mean BP were found in all cases at the 1 week ($p<0.01$), 2 week ($p<0.05$) and 4 week ($p<0.01$) periods compared to the pre-values, respectively (See FIG. 5). Significant increase in sodium removals were found in the day on low sodium dialysate in all cases ($p<0.001$) (See FIG. 6). Serum sodium levels were decreased significantly at the 1 week ($p<0.01$), 2 week ($p<0.05$) and 3 week ($<0.05$) periods compared to the pre-values, respectively (See FIG. 7). Plasma osmolality were decreased at the 1 week and 2 week periods significantly ($p<0.05$, respectively) (See FIG. 8). Significant decrease in ANP levels were found at 1 week ($p<0.05$) (See FIG. 9), while significant decrease in c-GMP levels were found at the 1 week and 2 week periods ($p<0.05$, respectively) (See FIG. 10). On the other hand, significant increase in PRA was found at 1 week ($p<0.05$) (See FIG. 11).

edema revealed before the study in all cases were improved or decreased in seven of the patients at the end of the study.

Discussion

In order to study the clinical effect of lower sodium concentration dialysate, 120 mEq/l sodium dialysate was applied to patients instead of the standard dialysate (Na:132 mEq/l). As a result, no changes were found in body weight, nor TDV. However, significant fall in BP were found, and significant increase in transperitoneal sodium removals were achieved after starting the low sodium dialysate. The changes in ANP and its second-messager, c-GMP levels, reflect the intra-atrial pressure and volume expansion even in patients with end-stage renal failure. Therefore, the decreased levels in ANP and c-GMP found in patients, may suggest the improvement of intra-vascular volume overload in these cases, and may explain the fall in BP. The activation in PRA and the increase in PAC and NEp levels may result from the decrease of vascular volume and the fall in BP. Most patients noticed that their dry mouth decreased and they stopped excess water drinking. Supposedly, the fall of plasma osmolality partly produced the decrease of the dryness sensation of the mouth. Nonetheless, this was found even in patients who did not show the apparent decrease in plasma osmolality. Therefore, it is suggested that the relief of over-loaded sodium could suppress the increase in plasma osmolality, and excess water drinking.

Thus, low sodium dialysate (120 mEq/l) can effectively be used for the correction of overhydration, and the control of hypertension.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A peritoneal dialysis solution for providing a sustained osmotic gradient comprising:

an osmotic agent having at least one amino acid; and
   sodium in a concentration that is less than a sodium plasma concentration in a renal patient who is to receive the solution.

2. The peritoneal dialysis solution of claim 1 wherein the solution has a total osmolality of 300 to about 500.

3. The peritoneal dialysis solution of claim 1 wherein the sodium comprises approximately 35 to about 125 (meq/L).

4. The peritoneal dialysis solution of claim 1 wherein the osmotic agent has a osmolality of not more than 200 (mosm/L) and the solution further comprises:

0.0 to about 4.0 (% w/v) dextrose;

0 to about 120 (mEq/L) sodium;

0 to about 100 (mEq/L) chloride;

0 to about 45 (mEq/L) lactate;

0 to about 45 (mEq/L) bicarbonate;

0.0 to about 4.0 (mEq/L) calcium; and 0.0 to about 4.0 (mEq/L) magnesium.

5. A method for reducing the risk of hypertension comprising the step of administering to a hypertensive dialysis patient a peritoneal dialysis solution comprising an osmotic agent having at least one amino acid and sodium in a concentration that is less than the sodium concentration in the hypertensive dialysis patient who is to receive the solution.

6. The method of claim 5 wherein the peritoneal dialysis solution comprises:

0.0 to about 4.0 (% w/v) dextrose;

0 to about 120 (meq/L) sodium;

0 to about 100 (meq/L) chloride;

0 to about 45 (meq/L) lactate;

0 to about 45 (meq/L) bicarbonate;

0.0 to about 4.0 (meq/L) calcium; and 0.0 to about 4.0 (meq/L) magnesium.

7. The method of claim 5 wherein the peritoneal dialysis solution has a total osmolality of 300 to about 500.

8. The method of claim 5 wherein the sodium comprises approximately 35 to about 125 (meq/L).

9. The method of claim 5 wherein the osmotic agent has an osmolality of not more than 200 mOsm/L and the solution further comprises:

0.0 to about 4.0 (% w/v) dextrose;

0 to about 120 (meq/L) sodium;

0 to about 100 (meq/L) chloride;

0 to about 45 (meq/L) lactate;

0 to about 45 (meq/L) bicarbonate;

0.0 to about 4.0 (meq/L) calcium; and 0.0 to about 4.0 (meq/L) magnesium.

* * * * *

UNITED STATES PATENT AND TRADEMARK OFFICE
CERTIFICATE OF CORRECTION

PATENT NO. : 5,629,025

DATED : May 13, 1997

INVENTOR(S) : Ty Shockley, et al.

It is certified that error appears in the above-identified patent and that said Letters Patent is hereby corrected as shown below:

Column 8, Line 31: delete "35" and insert --3.5--

Column 8, Line 33: delete "15" and insert --1.5--

Column 8, Table No. 1, Solution 11, at Column labeled Total Osm: delete "926" and insert --326--

Column 8, Table No. 1, Solution 12, at Column labeled Total Osm: delete "348" and insert --346--

Column 8, Table No. 1, Solution 14, at Column labeled Total Osm: delete "358" and insert --356--

Column 9, Line 32: delete "(NNAD)" and insert --(NNaD)--

Signed and Sealed this

Second Day of December, 1997

Attest:

Attesting Officer

BRUCE LEHMAN

Commissioner of Patents and Trademarks